United States Patent [19]
Gutcho et al.

[11] 4,139,604
[45] Feb. 13, 1979

[54] SEPARATION TECHNIQUE FOR ASSAYS

[75] Inventors: Sidney Gutcho, Monsey, N.Y.; Joan K. Givas, Crystal Lake, Ill.

[73] Assignee: Becton, Dickinson and Company, Rutherford, N.J.

[21] Appl. No.: 833,722

[22] Filed: Sep. 16, 1977

[51] Int. Cl.² .............................................. A61K 43/00
[52] U.S. Cl. ...................... 424/1; 23/230 B; 23/230.3; 424/1.5; 424/12; 23/915; 23/920
[58] Field of Search ............... 23/230 B, 230.3; 424/1, 424/12, 1.5

[56] References Cited
U.S. PATENT DOCUMENTS

| | | | |
|---|---|---|---|
| 3,920,580 | 11/1975 | Mast | 23/230 B |
| 3,925,020 | 12/1975 | Ogawa et al. | 424/1 |
| 3,933,997 | 1/1976 | Hersh et al. | 23/230 B |
| 4,018,564 | 4/1977 | Wright | 23/230 B |

Primary Examiner—Leland A. Sebastian
Attorney, Agent, or Firm—Marn & Jangarathis

[57] ABSTRACT

In an assay wherein radiolabeled substance bound to a receptor is separated from unbound radiolabeled substance, such separation is effected by the use of a combination of a particulate adsorbent and a thickening agent to decrease adsorption time. The procedure can be employed, for example, in separating bound iron from free iron in a total or unsaturated iron binding capacity assay.

9 Claims, No Drawings

SEPARATION TECHNIQUE FOR ASSAYS

This invention relates to assays, and more particularly, to an improvement in the procedure for separating a labeled substance bound to a receptor from unbound labeled substance in such assays by the use of a particulate adsorbent.

In many assays which employ a labeled substance, in particular, a radiolabeled substance, the assay procedure involves separation of labeled substance bound to a receptor from unbound labeled substance by adsorption of the unbound labeled substance on a particulate adsorbent. Thus, for example, in many assays for a ligand based on competitive binding for a limited number of receptor sites between the labeled and unlabeled form of the ligand, the separation of bound labeled ligand and unbound labeled ligand is effected by the use of a particulate adsorbent. Similarly, in serum iron assays (both unsaturated and total iron binding capacity assays), radioactive iron bound to transferrin is separated from unbound radioactive iron by adsorbing the unbound radioactive iron on a particulate adsorbent.

The present invention is directed to an improvement in the procedure for separating a bound labeled substance from unbound labeled substance by the use of a particulate adsorbent.

In accordance with the present invention, there is provided an improved assay wherein bound labeled substance is separated from unbound labeled substance from a solution containing same by the addition of a particulate adsorbent for the unbound labeled substance and a thickening agent to maintain the adsorbent in suspension, followed by separation of the adsorbent containing adsorbed unbound labeled substance and thickening agent from the solution. Applicant has found that the addition of a thickening agent improves the ability of the adsorbent to adsorb unbound labeled substance from the solution.

The thickening agent which is employed in accordance with the present invention is a thickening agent which maintains the particulate adsorbent in suspension in the solution; i.e., the thickening agent increases the viscosity of the solution. As representative examples of suitable thickening agents, there may be mentioned: fumed silica; cellulose polymers, such as carboxymethylcellulose, hydroxymethylcellulose, methyl cellulose, hydroxypropyl cellulose; etc.; natural polymers, such as, low molecular weight gelatin, guar gum, tragacanth, acacia (gum arabic); water soluble starch, etc; organic compounds, such as sorbitol, dextran, glycerin, propylene glycol, etc. A preferred thickening agent is a fumed silica.

The solid particulate adsorbent which is used for separating bound and free labeled substance may be any one of the wide variety of solid adsorbents which are known in the art. As representative examples of such adsorbents, there may be mentioned: ion exchange resins, charcoal (coated and uncoated), inorganic solids, such as bentonite, talc, precipitated silica; etc. The selection of a suitable particulate adsorbent for a particular assay is deemed to be within the scope of those skilled in the art from the teachings herein.

The thickening agent and adsorbent are employed in relative proportions suitable for maintaining the adsorbent suspended in the assay solution. In general, the weight ratio of the thickening agent to adsorbent is from 1:0.25 to 1:40, and preferably from 1:1 to 1:5.

The present invention is applicable to any one of a wide variety of assays for any one of a wide variety of ligands for which an appropriate receptor can be found, such as (1) antigens, which when introduced into the blood stream of a vertebrate, result in the formation of antibodies; (2) haptens, which when bound to an antigenic carrier and introduced into the blood stream of a vertebrate produce antibodies specific for the hapten or (3) ligands which have naturally occurring receptors which can be isolated in a form specific for the ligand. The present invention is also applicable to an assay for measuring total iron binding capacity and/or unsaturated iron binding capacity by the use of radioactive iron as the labeled substance.

As representative examples of ligands which can be assayed by competitive protein binding with the separation of bound and free labeled ligand being effected in accordance with the invention, there may be mentioned: polypeptides, nucleotides, nucleosides and proteins, such as ACTH, oxytocin, lutenizing hormone, insulin, proinsulin, Bence-Jones protein, chorionic gonadotropin, pituitary gonadotropin, growth hormone, renin, thryoxine binding globulin, bradykinin, angiotensin, follicle stimulating hormone; cyclic AMP; cholylglycine, cyclic GMP, etc.; steroids, including: estrogens, gestrogens, androgens, adrenocortical hormones, bile acids, cardiotonic glycosides, aglycones as well as saponins. As specific examples, there may be mentioned: thyroxine, triiodothyronine, testosterone, androsterone, equilenin, estrone, estriol, progesterone, pregnenolone, 17-hydroxydioxycorticosterone (compound S), deoxycorticoserone, cortisone, corticosterone, cortisol, aldosterone, digoxin, digitoxin, etc.; vitamins, such as folic acid, the B vitamin group, the D vitamins, and miscellaneous ligands, such as, antigens for Viral Hepatitis A and B, Rubella, Herpes Simplex, $\alpha$-fetoprotein, etc. It is to be understood that the labeled ligand, in many cases, is employed in the assay as an appropriate analog and the term labeled form of the ligand includes such analogs.

The "label", "tag" or "tracer" (such terms are interchangeably used in the art) can be a radioisotope, an enzyme, a fluorescent material, etc., with a radioisotope being preferred, such as radioactive iodine, tritium, cobalt, iron, etc. The use of such labels or tags is known in the art and no further details are necessary for an understanding of the invention.

In a radioassay for a ligand, a sample containing an unknown quantity of ligand, is combined with a known quantity of radiolabeled ligand and known quantity of receptor and the percentage of the labeled form bound to the receptor will depend upon the quantity of ligand present in the sample. A particulate adsorbent for the unbound radiolabeled ligand and thickening agent are added to the sample, with the thickening agent maintaining the solid adsorbent in suspension to thereby enhance the adsorption of unbound labeled ligand. It is to be understood that unbound ligand which is not radiolabeled is also adsorbed. The adsorbent, containing adsorbed unbound ligand, and thickening agent are then separated from the sample; e.g., by centrifugation. The amount of labeled ligand remaining in the sample (bound) and/or the amount of radiolabeled ligand separated from the sample (unbound) is determined and compared with a standard curve, as known in the art.

In a total iron binding capacity assay, iron is dissociated from the transferrin receptor by lowering the pH of the serum sample to below 5, followed by the addition of a known amount of iron, including radioactive iron($^{59}$Fe), in excess of the amount required to occupy all of the binding sites. The sample is then made alkaline to effect binding of the iron to the transferrin, and as a result of the fact that there is excess iron present, all of the binding sites are occupied and unbound or free iron remains in the sample. A particulate adsorbent in particular, an ion exchange resin, and a thickening agent are added to the sample to effect adsorption of the unbound iron, followed by centrifugation to pelletize the adsorbent, containing adsorbed unbound iron, and thickening agent. The supernatant containing the bound iron is decanted and counted in a solid crystal scintillation counter and the total iron binding capacity determined from such data by procedures known in the art.

The unsaturated iron binding capacity is determined by adding, at an alkaline pH, a known amount of radioactive iron which is in excess of that required to occupy the remaining iron binding sites of the samples. A particulate adsorbent and thickening agent are then added to the sample for separation of unbound iron, as hereinabove described with reference to the total iron binding capacity assay. The supernatant is counted, and the unsaturated iron binding capacity determined from the counts by procedures known in the art.

The serum iron content may be determined by subtracting the unsaturated iron binding capacity from the total iron binding capacity.

The invention will be further described with respect to the following examples; however, the scope of the invention is not to be limited thereby.

EXAMPLE

The following reagents are employed:
(1) [$^{59}$Fe] reaction solution — 15.00 μg/ml iron and [$^{59}$Fe] (0.62μ Ci/ml) and 0.6% citric acid monohydrate.
(2) Sodium carbonate solution — 0.86% w/v aqueous sodium carbonate
(3) Resin Suspension — 1.25% w/v of the ion exchange resin Amberlite IRP 67M resin and 0.5% of fumed silica (Cab-o-Sil grade M-5) suspending agent.

Treat all tubes similarly from this point.
7. Incubate all tubes at room temperature for 5 minutes. Number a duplicate set of tubes (except total tubes). This may also be done conveniently at step 1. Set aside until step 12.
8. Add 800 μl Resin Suspension to blank and sample tubes; do not add to total tubes. This reagent is "squirted" into each tube to obtain a uniform suspension in the reaction mixture.
9. Let stand at room temperature for 5 minutes from the time of the last addition in step 8.
10. Centrifuge blanks and sample tubes for 5 minutes at a speed of at least 1240xg.
11. Gently decant each supernatant from blank and sample tubes into a similarly numbered clean tube. Maximal transfer is obtained by gently hitting the rims together. Do not decant over any resin. Discard the resin residues.
12. Count the radioactivity in the tubes into which the supernatants have been decanted for at least 1 minute in a solid crystal scintillation counter (gamma counter). Include the total tubes. All tubes must be counted for the same period of time.

For ease of calculation of sample results from the counting data, place the tubes in the gamma counter in the following sequence: blank tubes, total tubes, UIBC tubes for serum sample number 1 (tube U1, U1), TIBC tubes for serum sample number 1 (T1, T1) and so on with each set of UIBC tubes followed by the corresponding set of TIBC tubes.

The present invention is particularly advantageous in that it is possible to effect adsorption of a free labeled substance onto a particulate adsorbent without the use of a rotator or frequent manual mixing. The adsorption is effected rapidly, in some cases essentially instantaneously, thus effecting a time savings. In addition, the use of a thickening agent aids in the packing of the centrifuged adsorbent thus shortening the time for separating the supernatant by decantation.

Numerous modifications and variations of the present invention are possible in light of the above teachings and, therefore, within the scope of the appended claims,

PROTOCOL

| TIBC | UIBC |
|---|---|
| 1. Number two tubes for each sample:<br>T1, T1, T2, T2, T3, T3, etc. | 1. Number two tubes for each sample<br>U1, U1, U2, U2, U3, U3, etc.<br>Also mark two blanks and two total tubes. |
| 2. Add 200μl patient serum to all sample tubes (TIBC and UIBC) 200μl water to each blank tube and 1000μl water to each total tube: | |

| Tube | Serum | Water |
|---|---|---|
| T1, T2, T3 | 200μl | — |
| U1, U2, U3 | 200μl | — |
| Blank | — | 200μl |
| Total | — | 1000μl |

3. Add 200μl [$^{59}$Fe] Reaction Solution to the TIBC tubes. Mix well.

4. Hold all tubes at room temperature for 10 minutes.
5. Add 200μl Sodium Carbonate Solution to all tubes. Mix well.

6. Add 200μl [$^{59}$Fe] Reaction Solution to the UIBC, blank and total tubes. Mix well. Set total tubes aside until step 12.

the invention may be practiced otherwise than as particularly described.

What is claimed is:

1. In a liquid phase assay wherein bound labeled substance is separated from unbound labeled substance, the improvement comprising:
   adding to a solution containing bound labeled substance and unbound labeled substance a particulate adsorbent for the substance and a thickening agent different than the adsorbent which increases the viscosity of the solution to maintain the adsorbent in suspension in the solution; and
   separating solution containing bound labeled substance from the thickening agent and adsorbent containing adsorbed unbound labeled substance.

2. The process of claim 1 wherein the assay is a radioassay.

3. The process of claim 2 wherein the assay is a radioassay for iron.

4. The process of claim 3 wherein the weight ratio of thickening agent to adsorbent is from 1:0.25 to 1:40.

5. The process of claim 4 wherein the particulate adsorbent is an ion exchange resin.

6. The process of claim 5 wherein the thickening agent is fumed silica.

7. The process of claim 2 wherein the thickening agent is selected from the group consisting of fumed silica, cellulose polymers; natural polymers, sorbitol, dextran, glycerin and propylene glycol.

8. The process of claim 2 wherein the weight ratio of suspending agent to adsorbent is from 1:0.25 to 1:40.

9. The process of claim 8 wherein the weight ratio is from 1:1 to 1:5.

* * * * *